US009597275B2

(12) United States Patent
Hattori et al.

(10) Patent No.: US 9,597,275 B2
(45) Date of Patent: Mar. 21, 2017

(54) GELLANT

(71) Applicant: AJINOMOTO CO., INC., Tokyo (JP)

(72) Inventors: Gaku Hattori, Kawasaki (JP); Masahiro Ino, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/945,839

(22) Filed: Nov. 19, 2015

(65) Prior Publication Data

US 2016/0074304 A1    Mar. 17, 2016

Related U.S. Application Data

(63) Continuation of application No. PCT/JP2014/063237, filed on May 19, 2014.

(30) Foreign Application Priority Data

May 20, 2013    (JP) ................................. 2013-106604

(51) Int. Cl.

| | |
|---|---|
| A61K 8/64 | (2006.01) |
| A61Q 1/06 | (2006.01) |
| A61Q 15/00 | (2006.01) |
| C09K 3/00 | (2006.01) |
| A61K 8/02 | (2006.01) |
| A61K 8/04 | (2006.01) |
| A61Q 1/08 | (2006.01) |
| C07K 5/072 | (2006.01) |

(52) U.S. Cl.
CPC .............. *A61K 8/64* (2013.01); *A61K 8/0216* (2013.01); *A61K 8/0229* (2013.01); *A61K 8/042* (2013.01); *A61Q 1/06* (2013.01); *A61Q 1/08* (2013.01); *A61Q 15/00* (2013.01); *C07K 5/06104* (2013.01); *C07K 5/06113* (2013.01); *C09K 3/00* (2013.01); *A61K 2800/592* (2013.01)

(58) Field of Classification Search
None
See application file for complete search history.

(56) References Cited

U.S. PATENT DOCUMENTS

| | | |
|---|---|---|
| 2004/0248812 A1 | 12/2004 | Hanabusa et al. |
| 2005/0208085 A1 | 9/2005 | Yamato et al. |
| 2006/0078581 A1 | 4/2006 | Yamato |
| 2007/0185208 A1 | 8/2007 | Miyajima et al. |
| 2007/0237732 A1 | 10/2007 | Yamato et al. |
| 2008/0280865 A1 | 11/2008 | Tobita |
| 2008/0311164 A1 | 12/2008 | Saito et al. |
| 2013/0203687 A1 | 8/2013 | Miyachi et al. |

FOREIGN PATENT DOCUMENTS

| | | |
|---|---|---|
| CN | 1659251 A | 8/2005 |
| CN | 101283960 A | 10/2008 |
| CN | 101365415 A | 2/2009 |
| CN | 101743289 A | 6/2010 |
| EP | 1 473 027 A1 | 11/2004 |
| JP | 2000-44554 A | 2/2000 |
| JP | 2005-281292 A | 10/2005 |
| JP | 2005-298388 A | 10/2005 |
| JP | 2006-225403 A | 8/2006 |
| JP | 2007-186498 A | 7/2007 |
| WO | WO 2004/105707 A1 | 12/2004 |

OTHER PUBLICATIONS

Combined Chinese Office Action and Search Report issued Sep. 23, 2016 in Patent Application No. 201480029346.2 (with partial English translation and English translation of categories of cited documents).
Extended European Search Report dated Sep. 20, 2016 issued in corresponding European patent application No. 14801229.7.

*Primary Examiner* — Jeanette Lieb
(74) *Attorney, Agent, or Firm* — Oblon, McClelland, Maier & Neustadt, L.L.P.

(57) ABSTRACT

The present invention provides a novel gellant capable of favorably gelatinizing an oily base.
The present invention relates to a gellant for an oily base, which contains the peptide compound represented by the formula (1), and further relates to a gelatinous composition containing (A) the gellant for an oily base, and (B) an oily base.
Formula (1):

(1)

wherein the symbols are as described in the DESCRIPTION.

26 Claims, No Drawings

GELLANT

CROSS REFERENCES TO RELATED APPLICATIONS

This application is a continuation of International Patent Application No. PCT/JP2014/063237, filed on May 19, 2014, and claims priority to Japanese Patent Application No. 2013-106604, filed on May 20, 2013, all of which are incorporated herein by reference in their entireties.

BACKGROUND OF THE INVENTION

Field of the Invention

The present invention relates to a gellant for an oily base. More particularly, the present invention relates to a gellant for an oily base, which contains a particular peptide compound. The gellant of the present invention is useful for gelatinizing an oily base in a liquid form at ambient temperature to diversify the form thereof.

Discussion of the Background

As a gellant for an oily base, conventionally, 12-hydroxystearic acid, dextrin palmitate, and a condensate of aromatic aldehyde and polyvalent alcohol represented by dibenzylidene-D-sorbitol, and the like are generally known. To sufficiently gelatinize an oily base, however, these gellants need to be added in a large amount, which problematically impairs the texture of the oily base and the like.

On the other hand, it has been found in recent years that a gemini (twins) type amphiphilic compound having 2 chains and 3 hydrophilic groups and using natural fatty acid and amino acid as starting materials has an oily gel formation function (see patent documents 1, 2). This compound is useful since it has a peptide structure (containing two glutamic acids and one lysine), due to which it has an oily gel formation function, as well as a superior skin care function, a hair care function and the like. In addition, there are high needs for compounds obtained from naturally occurring materials such as amino acid, peptide and the like from the aspects of safety and natural preference which is increasing in recent years.

Therefore, a gellant for an oily base, which has a peptide structure and a superior gelling ability, has been desired.

DOCUMENT LIST

Patent Documents patent document 1: JP-A-2006-225403
patent document 2: JP-A-2007-186498

SUMMARY OF THE INVENTION

Problems to be Solved by the Invention

The problem of the present invention is to provide a novel gellant capable of finely gelatinizing an oily base.

Means of Solving the Problems

The present inventors have conducted intensive studies in view of the above-mentioned problems and found that a particular peptide compound has a superior gelatinization ability, which resulted in the completion of the present invention. More surprisingly, they have found that the novel gellant can suppress what is called a "sweating phenomenon" wherein a gelatinized oily base oozes out from the surface of a gelatinous composition due to time course changes.

Accordingly, the present invention includes the following embodiments.

[1] A gellant for an oily base comprising a peptide compound represented by the formula (1):

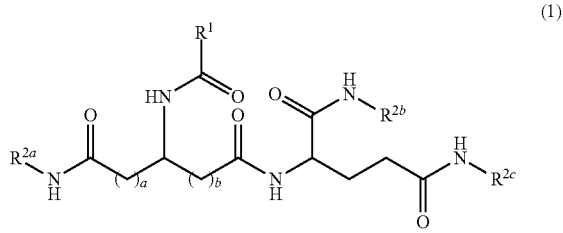

[in the formula (1), $R^1$, $R^{2a}$, $R^{2b}$ and $R^{2c}$ are each an alkyl group, a and b are each an integer of 0 or 2, (a,b)=(0,2) or (a,b)=(2,0)].

[2] The gellant of the above-mentioned [1], wherein $R^1$ is an alkyl group having 3-21 carbon atoms, and $R^{2a}$, $R^{2b}$ and $R^{2c}$ are each an alkyl group having 1-10 carbon atoms.

[3] The gellant of the above-mentioned [1] or [2], wherein $R^1$ is a 1-ethylpentyl group or undecyl group, and $R^{2a}$, $R^{2b}$ and $R^{2c}$ are each a butyl group.

[4] A gelatinous composition comprising (A) the gellant for an oily base of any of the above-mentioned [1]-[3], and (B) an oily base.

[5] The gelatinous composition of the above-mentioned [4], wherein (B) the oily base is one or more kinds selected from the group consisting of silicone oil, ester oil, hydrocarbon, higher alcohol, and fatty acid.

[6] The gelatinous composition of the above-mentioned [4] or [5], wherein the amount of (A) as the amount of the peptide compound represented by the formula (1) is 0.01-20 mass % relative to the total amount of the gelatinous composition.

[7] The gelatinous composition of any of the above-mentioned [4]-[6], having a rod-shaped form.

[8] The gelatinous composition of any of the above-mentioned [4]-[7], which is an antiperspirant, lipstick or rouge.

Effect of the Invention

The gellant for an oily base of the present invention can favorably gelatinize an oily base with a small amount thereof, and can suppress what is called a "sweating phenomenon" wherein an oily base oozes out from the surface of a gelatinous composition. Also, since it has a peptide structure, a superior skin care function, and hair care function can be expected.

DETAILED DESCRIPTION OF THE PREFERRED EMBODIMENTS

The gellant for an oily base of the present invention contains a particular peptide compound.

In the present specification, "a gellant" refers to a substance or composition that thickens a liquid, and changes same to a jelly state or solid state. In the present invention, it is particularly useful as a gellant for oily liquids (oily bases).

[Peptide Compound]

A peptide compound contained in the gellant for an oily base of the present invention is a compound represented by the formula (1).

Formula (1):

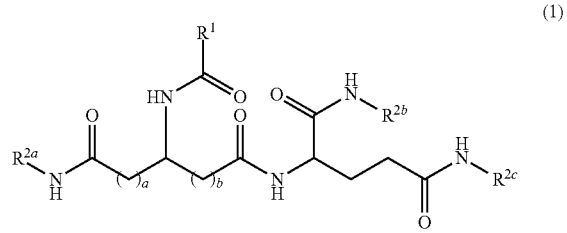

[in the formula (1), $R^1$, $R^{2a}$, $R^{2b}$ and $R^{2c}$ are each an alkyl group, a and b are each an integer of 0 or 2, and (a,b)=(0,2) or (a,b)=(2,0)]

In the formula (1), the alkyl group for $R^1$ may be a straight chain or branched chain, and is preferably an alkyl group having 3-21 carbon atoms.

Examples of the alkyl group include propyl group, isopropyl group, butyl group, isobutyl group, sec-butyl group, tert-butyl group, pentyl group, sec-pentyl group, tert-pentyl group, isopentyl group, hexyl group, heptyl group, 1-ethylpentyl group, octyl group, 2-ethylhexyl group, tert-octyl group, nonyl group, isononyl group, decyl group, isodecyl group, undecyl group, dodecyl group, tridecyl group, isotridecyl group, tetradecyl group, pentadecyl group, hexadecyl group, octadecyl group, isooctadecyl group, 2-heptylundecyl group, icosyl group, henicosyl group and the like. Since an effective gel strength can be imparted with a small amount, an alkyl group having 5-17 carbon atoms is more preferable, an alkyl group having 7-13 carbon atoms is still more preferable, and a 1-ethylpentyl group or undecyl group is most preferable.

In the formula (1), an alkyl group for $R^{2a}$, $R^{2b}$ or $R^{2c}$ may be any of a straight chain and a branched chain, and may be the same or different. As an alkyl group for $R^{2a}$, $R^{2b}$ or $R^{2c}$, an alkyl group having 1-10 carbon atoms is preferable.

Examples of the alkyl group include methyl group, ethyl group, isopropyl group, propyl group, butyl group, isobutyl group, sec-butyl group, tert-butyl group, pentyl group, sec-pentyl group, tert-pentyl group, isopentyl group, hexyl group, heptyl group, octyl group, 2-ethylhexyl group, tert-octyl group, nonyl group, isononyl group, decyl group, isodecyl group and the like. Since an effective gel strength can be imparted with a small amount thereof, an alkyl group having 3-6 carbon atoms is more preferable, and each of the alkyl groups for $R^{2a}$, $R^{2b}$ and $R^{2c}$ is still more preferably a butyl group.

In the formula (1), a and b are each an integer of 0 or 2, and (a,b)=(0,2) or (a,b)=(2,0). That is, when a is 0, b is 2, and when a is 2, b is 0.

The peptide compound represented by the formula (1) has an asymmetric carbon on an amino acid residue, but a DL form ratio (D form/L form (mass/mass)) based on the asymmetric carbon is not particularly determined.

The peptide compound represented by the formula (1) can be produced by a method known per se and using N-acyl glutamic anhydride, glutamate and alkylamine.

[Gellant for Oily Base]

In the present invention, a peptide compound represented by the above-mentioned formula (1) is directly used, or added with additives such as excipients (cetyl alcohol, stearyl alcohol, stearic acid, hydrogenated oil, solid paraffin and the like) and the like, and can be provided as a powdery gellant for an oily base. In addition, the aforementioned peptide compound is dissolved or suspended in a solvent such as ethanol, isopropanol, dipropylene glycol and the like, and can also be provided as a liquid or suspension-like gellant for an oily base. For the object of the present invention, it is preferably provided in the form of a powder.

The content of the peptide compound represented by the formula (1) is preferably 0.1 mass %-100 mass %, more preferably 1.0 mass %-100 mass %, relative to the total amount of the gellant for an oily base of the present invention.

The oily base that can be gelatinized by the gellant for an oily base of the present invention is not particularly limited as long as it is an oily base generally used for cosmetics and quasi-drugs. Examples thereof include silicone oil such as methyl polysiloxane, highly polymerized methyl polysiloxane, polyoxyethylene/methylpolysiloxane copolymer, polyoxypropylene/methylpolysiloxane copolymer, poly(oxyethylene, oxypropylene)/methylpolysiloxane copolymer, stearoxy methylpolysiloxane, stearoxy trimethylsilane, methylhydrogenpolysiloxane, octamethyl polysiloxane, decamethyl polysiloxane, decamethyl cyclopentasiloxane, octamethyl cyclotetrasiloxane, tetrahydrotetramethyl cyclotetrasiloxane, methylcyclopolysiloxane, dodecamethylcyclohexasiloxane, methylphenylpolysiloxane, trimethylsiloxy-silicic acid, aminoethyl aminopropyl siloxane/dimethylsiloxane copolymer, silanol-denatured polysiloxane, alkoxy-denatured polysiloxane, fatty acid-denatured polysiloxane, fluorine-denatured polysiloxane, epoxy-denatured polysiloxane, alkoxy-denatured polysiloxane perfluoropolyether, polyvinyl acetate dimethylpolysiloxane and the like; ester oil such as myristyl myristate, hexyl laurate, decyl oleate, isopropyl myristate, hexyldecyl dimethyl octanoate, glyceryl monostearate, glyceryl tri-2-ethylhexanoate, diethyl phthalate, ethylene glycol monostearate, octyl oxystearate, benzoic acid alkyl ester and the like; hydrocarbon such as liquid paraffin, polyisobutene, petrolatum, squalane and the like; higher alcohol such as cetyl alcohol, isostearyl alcohol, lauryl alcohol, hexyldecanol, octyldodecanol and the like; fatty acid such as isostearic acid, undecylenoic acid, oleic acid and the like; wax such as lanolin, hydrogenated lanolin, carnauba wax and the like; fats and oils such as mink oil, cacao oil, coconut oil, palm kernel oil, camellia oil, sesame oil, castor oil, olive oil and the like; ethylene/α-olefin/co-oligomer and the like.

As the oily base that can be gelatinized by the gellant for an oily base of the present invention, silicone oil, ester oil, hydrocarbon, higher alcohol, and fatty acid are preferable, and silicone oil, ester oil, hydrocarbon, and higher alcohol are more preferable.

[Gelatinous Composition]

The present invention further provides a gelatinous composition containing (A) a gellant for an oily base containing a peptide compound represented by the above-mentioned formula (1), and (B) an oily base.

Examples of the (B) oily base contained in the gelatinous composition of the present invention include the oily base described above, and one or more kinds selected from the oily base can be used.

For the object of the present invention, one or more kinds selected from the group consisting of silicone oil, ester oil, hydrocarbon, higher alcohol and fatty acid are preferably used, and one or more kinds selected from the group consisting of silicone oil, ester oil, hydrocarbon and higher alcohol are more preferably used.

The amount of the above-mentioned (A) gellant for an oily base in the gelatinous composition of the present invention is not particularly limited as long as the oily base is gelatinized. Since a gelatinous composition superior in the gel strength and the above-mentioned "sweating phenomenon" suppressive effect is obtained, the lower limit of the amount (mass %) of (A) gellant for an oily base relative to the total amount of the gelatinous composition is preferably 0.01 mass %, more preferably 0.03 mass %, further preferably 0.05 mass %, further more preferably 0.1 mass %, as the amount of the peptide compound represented by the above-mentioned formula (1). In addition, since a gelatinous composition having a superior sense of use is obtained, the upper limit of the amount (mass %) of (A) gellant for an oily base relative to the total amount of the gelatinous composition is preferably 20 mass %, more preferably 10 mass %, still more preferably 7 mass %, still further more preferably 5 mass %, most preferably 3 mass %, as the amount of the peptide compound represented by the above-mentioned formula (1).

The amount of the oily base of the above-mentioned (B) in the gelatinous composition of the present invention is not particularly limited as long as gelatinization proceeds. Since a gel network is formed and maintained, the lower limit of the amount (mass %) of the oily base of (B) relative to the total amount of the gelatinous composition is preferably 10 mass %, more preferably 20 mass %, still more preferably 30 mass %, still further preferably 50 mass %, most preferably 70 mass %. Since a gel can be formed efficiently, the upper limit of the amount (mass %) of the oily base of (B) relative to the total amount of the gel composition is preferably 99.99 mass %, more preferably 99.9 mass %, still more preferably 99 mass %, still further preferably 98 mass %.

The gelatinous composition of the present invention can contain components generally used for cosmetics such as various chelating agents, antiperspirant active ingredient, surfactant, various additives, various powders and the like within the range where the effect of the present invention is not inhibited.

In a narrow sense, a gelatinous composition in the present invention means a composition composed only of a gellant for an oily base of (A) and an oily base of (B) and, in a wide sense, it also means a cosmetics, aromatic, a quasi-drug and the like as a final product further containing the above-mentioned various additives.

While various chelating agents that can be added to the gelatinous composition of the present invention are not particularly limited, preferable examples include triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, aurintricarboxylic acid, xylenol orange, 5-sulfosalicylic acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid, acetylacetone, and salts thereof. One kind therefrom may be selected and used alone, or two or more kinds may be used in combination.

The antiperspirant active ingredient that can be added to the gelatinous composition of the present invention refers to a component that suppresses the development of sweat by strong astringent action on the skin. Examples of the antiperspirant active ingredient include chlorohydroxyaluminum, aluminum chloride, chlorohydroxyaluminum allantoinate, aluminum sulfate, zinc oxide, zinc paraphenolsulfonate, and zirconium aluminum complex produced by reacting zirconyl chloride with aluminum hydroxide and aluminum chlorohydroxide. One kind therefrom may be selected and used alone, or two or more kinds may be used in combination.

Examples of the surfactant that can be added to the gelatinous composition of the present invention include anionic surfactants such as N-long chain acyl amino acid salts (N-long chain acyl acidic amino acid salt, N-long chain acyl neutral amino acid salt and the like), N-long chain acyl-N-methyltaurine salt, alkylsulfate and alkylene oxide adduct thereof, fatty acid amide ether sulfate, metal salt or weak base salt of fatty acid, sulfosuccinic acid-based surfactant, alkyl phosphate and alkylene oxide adduct thereof, alkylethercarboxylic acid, and the like; non-ionic surfactants such as ether type surfactants (glycerol ether and alkylene oxide adduct thereof and the like), etherester type surfactants (alkylene oxide adduct of glycerol ester, alkylene oxide adduct of sorbitan ester and the like), ester type surfactants (polyoxyalkylene fatty acid ester, glycerol ester, fatty acid polyglycerol ester, sorbitan ester, sucrose ester of fatty acid and the like), alkyl glucosides, nitrogen-containing non-ionic surfactants (hydrogenated castor oil pyroglutamic acid diester and ethylene oxide adduct thereof, fatty acid alkanol amide and the like); cationic surfactants such as quaternary ammonium salts (alkyl ammonium chloride, dialkyl ammonium chloride and the like), aromatic quaternary ammonium salts (benzalkonium salt and the like), N-acylarginine ester, and the like; as well as amphoteric surfactants such as betaine type surfactants (alkylcarboxybetaine, alkylamidebetaine and the like), aminocarboxylic acid type surfactants (N,N-dialkylaminoalkylenecarboxylic acid and the like), imidazoline type surfactants (2-alkyl-1-hydroxyethyl-1-carboxymethylimidazolinium betaine and the like), amineoxide type surfactants (3-(lauroylamino)-N,N-dimethylpropane-1-amine N-oxide and the like), and the like.

One kind may be selected from the above-mentioned surfactants and added to the gelatinous composition of the present invention, or two or more kinds may be added in combination.

Examples of various additive that can be added to the gelatinous composition of the present invention include amino acids such as glycine, alanine, serine, threonine, arginine, glutamic acid, aspartic acid, isoleucine, leucine, valine and the like; polyvalent alcohol such as glycerol, ethylene glycol, 1,3-butylene glycol, propylene glycol, isoprene glycol and the like; water-soluble polymer such as polyamino acid containing polyglutamic acid, polyaspartic acid and a salt thereof, polyethylene glycol, gum arabic, alginates, xanthan gum, hyaluronic acid, hyaluronic acid salt, chitin, chitosan, water-soluble chitin, carboxyvinyl polymer, carboxymethyl cellulose, hydroxyethyl cellulose, hydroxypropyl trimethylammonium chloride, polychlorodimethylmethylene piperidium, polyvinylpyrrolidone derivative quaternary ammonium, cationized protein, collagen degradation products and a derivative thereof, acylated protein, polyglycerol, and the like; sugar alcohol such as mannitol and alkylene oxide adduct thereof; lower alcohol such as ethanol, propanol and the like, animals and plants extract, nucleic acid, vitamin, enzyme, anti-inflammatory agent, antimicrobial agent, preservative, antioxidant, UV absorber, dye, lake pigment, oxidation dye, pH adjuster, pearl agent, wetting agent and the like.

In the present invention, one or more kinds from the above-mentioned additives can be selected and used as necessary.

Examples of the various powders include organic powders, for example, resin powders such as nylon powder, nylon beads, silicone beads and the like, metal fatty acid soap, acylamino acids such as acyllysine, acylglutamic acid, acylarginine, acylglycine and the like, and the like; inorganic pigments such as yellow iron oxide, red iron oxide, black iron oxide, chrome oxide, cobalt oxide, carbon black, ultramarine blue, iron blue, zinc oxide, titanium oxide, zirconium oxide, silicon oxide, aluminum oxide, cerium oxide, micatitanium, boron nitride, barium sulfate, calcium carbonate, magnesium carbonate, aluminum silicate, magnesium silicate, silicon carbide, sericite, mica, talc, kaolin, plate-shaped barium sulfate, butterfly-shaped barium sulfate, titanium oxide fine particles, zinc oxide fine particles, iron oxide fine particles and the like, and the like, which may be further subjected to a surface treatment such as silicone treatment, fluorine compound treatment, silane coupling agent treatment, silanized organic titanate treatment, acylated lysine treatment, fatty acid treatment, metal soap treatment, oil treatment, amino acid treatment and the like.

In the present invention, one or more kinds from the above-mentioned powders can be selected and used as necessary.

While the form of the gelatinous composition of the present invention is not particularly limited, it can be provided as, for example, semi-solid such as paste, cream and the like, or a solid form such as granule, rod-shape, sphere, sheet and the like, and particularly, it is preferably provided as a rod-shaped form.

The gelatinous composition of the present invention can be prepared by adding (A) gellant for an oily base to (B) oily base, heat-dissolving them, where necessary, adding other addition components, uniformly mixing them, filling the mixture in a container such as bottle, jar and the like, or a mold having a desired form such as rod and the like, and then cooling the mixture to room temperature.

In addition, a granular gelatinous composition can be prepared by pulverization of solidified gel, gelatinization of an oil drop emulsified in an aqueous phase and the like.

The present invention further provides cosmetics or a quasi-drug, which contains the above-mentioned gelatinous composition of the present invention, or which is the gelatinous composition of the present invention itself.

The shape and size of the cosmetics and quasi-drug of the present invention may be any. In particular, they are provided as antiperspirant, facial wash, cleansing gel, skin milk, massage cream, cold cream, moisture gel, facial mask, aftershave gel, foundation, lipstick, rouge, cheek, mascara, shampoo, rinse, hair-growth drug, hair treatment, hair conditioner, tic, set lotion, hair cream, hair wax, hair mousse, permanent wave solution, hair dye, hair coloring, hair manicure, sunscreen oil, hand soap, aromatic, fomentation and the like. It is preferably provided as cosmetic or quasi-drug having a rod-shaped form.

EXAMPLES

The present invention is now explained in more detail in the following by referring to Examples, which are not to be construed as limitative.

Synthetic Example 1

Synthesis of Peptide Compound

A peptide compound represented by the formula (2) was synthesized as follows.
formula (2):

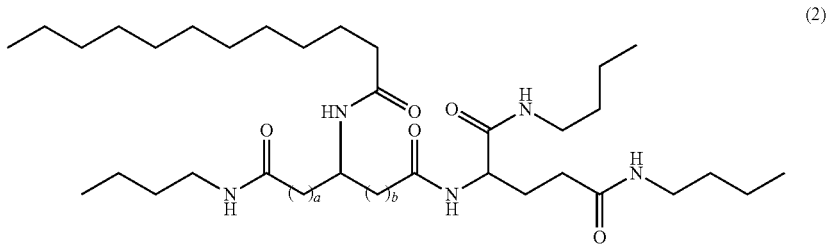

[in the formula (2), a and b is each an integer of 0 or 2, and (a,b)=(0,2) or (a,b)=(2,0)]

<Synthesis Method>

N-lauroyl-L-glutamic anhydride (31.1 g, 0.1 mol) was added to toluene (400 mL), and the mixture was dissolved by stirring at 95° C. Thereto was added sodium glutamate monohydrate (18.7 g, 0.1 mol), and the mixture was stirred with heating under reflux for 5 hr, and allowed to cool to room temperature. The mixture was adjusted to pH 1 with concentrated sulfuric acid, and the precipitated solid was filtered and dried to give 30.6 g of a solid (yield 67%). Then, the obtained solid (30.6 g, 0.067 mol) was suspended in methanol (300 mL), concentrated sulfuric acid (0.66 g, 0.0067 mol) was added, and the mixture was stirred with heating under reflux for 5 hr. Thereafter, methanol was evaporated under reduced pressure, butylamine (49 g, 0.67 mol) was added, and the solution was heated under reflux for 5 hr. Excess butylamine was evaporated under reduced pressure and the residue was washed with water and purified by chromatography to give the objective substance (41.8 g, yield 50%).

NMR:$^1$H-NMR peak (CD$_3$OD) δ:0.90-0.97 (m, 12H), 1.31-1.40 (m, 22H), 1.45-1.55 (m, 6H), 1.55-1.70 (m, 2H), 1.80-2.22 (m, 4H), 2.24-2.38 (m, 6H), 3.16-3.22 (m, 6H), 4.18-4.38 (m, 2H)

NMR measurement condition: Using nuclear magnetic resonance apparatus (manufactured by BRUKER, AVANCE 400), and is the measurement was performed with the peak of tetramethylsilane as 0 ppm.

<Evaluation of Gellant for Oily Base>
[Gelatinization Ability]

To cyclopentasiloxane/octyldodecanol (80/20 (mass ratio) mixture) [component (B)] (6 g) was added each gellant for an oily base of Example 1 and Comparative Examples 1-3 shown in Table 1 to 1 mass %, and the mixture was placed in a 30 mL sample tube bottle and dissolved by heating. After dissolution, the mixture was stood at room temperature at 25° C. for 24 hr to give a gelatinous composition. The gel strength of the obtained gelatinous composition was measured by a rheo meter (FUDOH RHEO METER NRM-2010-J-CW), and the gelatinization ability was evaluated by the following evaluation criteria. The adapter used was for plume, viscoelasticity, 109, and the stage speed was set to 6 cm/min. The results are shown in Table 1.

<Evaluation Criteria>

◯: gel strength of not less than 30 g

Δ: gel strength of not less than 1 g and less than 30 g x: no gelatinization

[Suppressive Action on Sweating Phenomenon]

In the same manner as above, a gelatinous composition was obtained, and the presence or absence of the development of a "sweating phenomenon", or a phenomenon of oozing out of an oily base from the surface of a gelatinous composition, in the obtained gelatinous composition was visually observed, and a suppressive action on the sweating phenomenon was evaluated by the following evaluation criteria. The results are shown in Table 1.

<Evaluation Criteria>

◯: sweating phenomenon is not observed x: sweating phenomenon is observed

Component (A) and component (B) used for this experiment were as follows.

(i) dilauroylglutamyl lysine sodium: manufactured by Asahi Kasei Chemicals Corporation, "Pellicer L-30"

(ii) dextrin palmitate: manufactured by Chiba Flour Milling Co., Ltd., "Rheopearl LK2"

(iii) 12-hydroxystearic acid: manufactured by Tokyo Chemical Industry Co., Ltd., reagent (iv) cyclopentasiloxane: manufactured by Toray•Dow Corning Corporation, "SH245"

(v) octyldodecanol: manufactured by Kokyu Alcohol Kogyo Co., Ltd., "Risonol 20SP"

TABLE 1

| Sample | Ex. 1 | Comp. Ex. 1 | Comp. Ex. 2 | Comp. Ex. 3 |
|---|---|---|---|---|
| gellant for oily base [component (A)] | peptide compound of Synthetic Example 1 | dilauroyl glutamic acid lysine sodium (compound described in JP-A-2006-225403) | dextrin palmitate | 12-hydroxy stearic acid |
| gelatinization ability | ◯ | x | x | x |
| sweating phenomenon | ◯ | — | — | — |

*; In Table, "—" means that observation of sweating phenomenon was not possible since the composition did not gelatinize.

As shown in Table 1, the gellant for an oily base of Example 1 of the present invention could form a gel having sufficient strength by the addition of 1 mass, and a gelatinous composition containing same suppressed a sweating phenomenon.

On the other hand, when an existing gellant for an oily base (Comparative Example 1-3) was added by 1 mass, gel was not formed.

That is, the gellant for an oily base of the present invention containing the peptide compound of Synthetic Example 1 could gelatinize an oily base by the addition of a small amount thereof as compared to other existing gellants for an oily base, and was confirmed to suppress the "sweating phenomenon".

INDUSTRIAL APPLICABILITY

The present invention can provide a gellant for an oily base, which can gelatinize an oily base by the addition of a small amount thereof, and suppress a "sweating phenomenon".

In addition, the present invention can provide a good gelatinous composition that suppresses a "sweating phenomenon".

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A gellant for an oily base, comprising at least one peptide compound represented by formula (1):

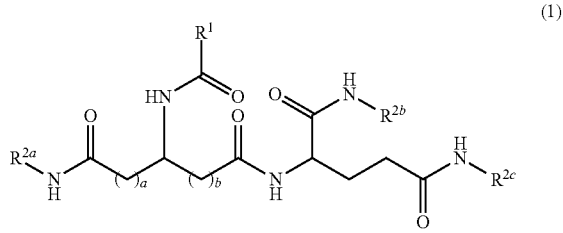

wherein $R^1$, $R^{2a}$, $R^{2b}$, and $R^{2c}$ are the same or different and are each independently an alkyl group, one of a and b is 0 and the other is 2.

2. A gellant according to claim 1, wherein $R^1$ is an alkyl group having 3 to 21 carbon atoms, and $R^{2a}$, $R^{2b}$ and $R^{2c}$ are the same or different and are each independently an alkyl group having 1 to 10 carbon atoms.

3. A gellant according to claim 1, wherein $R^1$ is a 1-ethylpentyl group or an undecyl group, and $R^{2a}$, $R^{2b}$ and $R^{2c}$ are each a butyl group.

4. A gellant according to claim 1, wherein a is 0 and b is 2.

5. A gellant according to claim 1, wherein a is 2 and b is 0.

6. A gelatinous composition, comprising:
(A) at least one gellant for an oily base according to claim 1; and
(B) an oily base.

7. A gelatinous composition, comprising:
(A) at least one gellant for an oily base according to claim 2; and
(B) an oily base.

8. A gelatinous composition, comprising:
(A) at least one gellant for an oily base according to claim 3; and
(B) an oily base.

9. A gelatinous composition according to claim 6, wherein (B) said oily base is at least one member selected from the group consisting of a silicone oil, an ester oil, a hydrocarbon, a higher alcohol, and a fatty acid.

10. A gelatinous composition according to claim 7, wherein (B) said oily base is at least one member selected from the group consisting of a silicone oil, an ester oil, a hydrocarbon, a higher alcohol, and a fatty acid.

11. A gelatinous composition according to claim 8, wherein (B) said oily base is at least one member selected from the group consisting of a silicone oil, an ester oil, a hydrocarbon, a higher alcohol, and a fatty acid.

12. A gelatinous composition according to claim 6, wherein said (A) at least one gellant is present in an amount, as the amount of the peptide compound represented by formula (1), of 0.01 to 20 mass %, based on the total amount of said gelatinous composition.

13. A gelatinous composition according to claim 7, wherein said (A) at least one gellant is present in an amount, as the amount of the peptide compound represented by formula (1), of 0.01 to 20 mass %, based on the total amount of said gelatinous composition.

14. A gelatinous composition according to claim 8, wherein said (A) at least one gellant is present in an amount, as the amount of the peptide compound represented by formula (1), of 0.01 to 20 mass %, based on the total amount of said gelatinous composition.

15. A gelatinous composition according to claim 6, which has a rod-shaped form.

16. A gelatinous composition according to claim 7, which has a rod-shaped form.

17. A gelatinous composition according to claim 8, which has a rod-shaped form.

18. A gelatinous composition according to claim 6, which is an antiperspirant, a lipstick, or a rouge.

19. A gelatinous composition according to claim 7, which is an antiperspirant, a lipstick, or a rouge.

20. A gelatinous composition according to claim 8, which is an antiperspirant, a lipstick, or a rouge.

21. A peptide compound represented by formula (1):

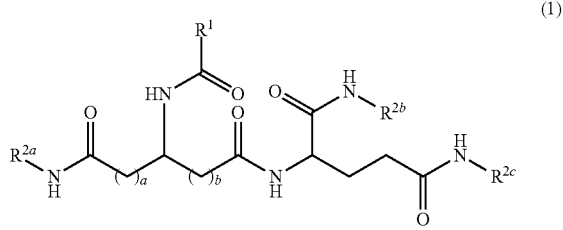

wherein $R^1$, $R^{2a}$, $R^{2b}$, and $R^{2c}$ are the same or different and are each independently an alkyl group, one of a and b is 0 and the other is 2.

22. A peptide compound according to claim 21, wherein $R^1$ is an alkyl group having 3 to 21 carbon atoms, and $R^{2a}$, $R^{2b}$ and $R^{2c}$ are the same or different and are each independently an alkyl group having 1 to 10 carbon atoms.

23. A peptide compound according to claim 21, wherein $R^1$ is a 1-ethylpentyl group or an undecyl group, and $R^{2a}$, $R^{2b}$ and $R^{2c}$ are each a butyl group.

24. A peptide compound according to claim 21, wherein $R^1$ is an undecyl group, and $R^{2a}$, $R^{2b}$ and $R^{2c}$ are each a butyl group.

25. A peptide compound according to claim 21, wherein a is 0 and b is 2.

26. A peptide compound according to claim 21, wherein a is 2 and b is 0.

* * * * *